United States Patent [19]

Brennan

[11] 3,997,621
[45] Dec. 14, 1976

[54] CONTROLLED OLIGOMERIZATION OF OLEFINS

[75] Inventor: James A. Brennan, Cherry Hill, N.J.

[73] Assignee: Mobil Oil Corporation, New York, N.Y.

[22] Filed: Mar. 17, 1975

[21] Appl. No.: 559,101

Related U.S. Application Data

[63] Continuation-in-part of Ser. No. 439,469, Feb. 4, 1974, abandoned, which is a continuation-in-part of Ser. No. 217,247, Jan. 17, 1972, Pat. No. 3,731,474.

[52] U.S. Cl. .................................. 260/683.15 B
[51] Int. Cl.² ........................................ C07C 3/18
[58] Field of Search ................... 260/683.15 B

[56] References Cited

UNITED STATES PATENTS

| | | | |
|---|---|---|---|
| 3,763,244 | 10/1973 | Shubkin | 260/683.15 B |
| 3,780,128 | 12/1973 | Shubkin | 260/683.15 B |

*Primary Examiner*—C. Davis
*Attorney, Agent, or Firm*—C. A. Huggett; M. G. Gilman

[57] ABSTRACT

Oligomerization of alpha olefins catalyzed by boron trifluoride is controlled to yield desired trimer as a dominant product by adding small amounts of ester together with water or alcohol promoter.

5 Claims, No Drawings

CONTROLLED OLIGOMERIZATION OF OLEFINS

CROSS-REFERENCE TO RELATED APPLICATIONS

Continuation-in-part of application Ser. No. 439,469, filed Feb. 4, 1974, now abandoned, which, in turn, is a continuation-in-part of application Ser. No. 217,247, filed Jan. 17, 1972, now U.S. Pat. No. 3,731,474. The disclosures of said prior applications are herewith incorporated herein by this reference.

BACKGROUND OF THE INVENTION

1. Field of the Invention

This invention relates to the oligomerization of olefins and relates more particularly to a reproducible process for varying the degree of oligomerization of 1-olefins with boron trifluoride catalyst. Still more particularly, in one of its aspects, the invention relates to an improved process for the oligomerization of olefins, or olefin fractions, for the manufacture of synthetic fluid lubricants, employing alcohol-promoted or water-promoted boron trifluoride catalysts, or mixtures of such catalysts, under conditions in which the degree of oligomerization can be controlled in order to obtain olefin oligomers suitable for use as synthetic fluid lubricants for many industrial applications, particularly as low temperature hydraulic fluid.

2. Description of the Prior Art

It has been shown that oligomers of olefins having 6 to 12 carbon atoms may be hydrogenated to yield synthetic lubricants. See Hamilton and Seger U.S. Pat. No. 3,149,178. The preferred olefins are linear alpha olefins and the dimer is preferably removed to a major extent when necessary in order to provide lubricants of low pour point and high fire and flash points.

The catalysts employed for oligomerization are generally of the Friedel-Crafts type, activated by water or a primary aliphatic alcohol. Other activators include phosphoric acid as in U.S. Pat. No. 3,742,082. Boron fluoride is a catalyst suited to that purpose when so activated. It is recognized that boron fluoride is essentially inactive in the pure state, although such activity has been reported for polymerization of the extremely reactive olefin isobutylene. Even in that case, there is controversy whether the boron fluoride system is perfectly dry, it being postulated by some writers that traces of moisture on the apparatus employed may be sufficient for water activation of the catalyst. Certainly, for the less reactive olefins such as those used for manufacture of synthetic lubricants, useful degree of oligomerization is achieved only with boron fluoride to which has been added a minor measurable quantity of an activator such as water or a primary alcohol.

It is reported in Holmes U.S. Pat. No. 2,384,916 that polymerization of isobutylene at extremely low temperatures, e.g. −78° C, in the presence of boron fluoride is promoted by certain oxygen-containing organic compounds, including low boiling esters. In accordance with Holmes teachings, the molecular weight of the product is increased in the range upwards of 100,000 by such promoter when the feed isobutylene is carefully freed from alcohol and the like by repeated distillations. See lines 67 to 71 of the first column on page 2.

SUMMARY OF THE INVENTION

According to the present invention, oligomers of 6 – 12 carbon atom olefins, preferably alpha olefins are produced under controlled conditions such that the product is suitable, upon hydrogenation, for use in such demanding products as hydraulic oils to be used at low temperatures, such as −40° F., encountered in aircraft. This and other like uses, require a fluid having a suitably high fire point and a low viscosity at the temperature of use, say below about 3000 centistokes Kinematic Viscosity (KV). It has been found, according to the invention, that this criterion is met for use at −40° F., when the product of oligomerizing an olefin such as decene-1 contains a high content of trimer ($C_{30}$). It is one important object of the invention to control the oligomerization to obtain the desirable product.

That objective is attained by oligomerization of the olefin feed with free boron fluoride in the presence of water or alcohol promoter and a minor amount of a low boiling ester of a carboxylic acid. The esters suitable for such use are the products of reaction between an aliphatic mono-hydric alcohol and a mono-carboxylic acid. On the basis of commercial availability, preference is had for the methyl and ethyl esters of carboxylic acids having two to five carbon atoms. Other esters may be used, other than formates which tend to decompose in the presence of boron fluoride, but are not seen to offer advantages which compensate for their greater cost.

In carrying out the above-described oligomerization as previously indicated, the ester of a carboxylic acid is employed as a modifier in combination with an alcohol-promoted, or water-promoted boron trifluoride catalyst, or mixtures thereof. In this respect, the reaction is carried out in a ratio of promoter to olefins of from about 0.001 moles to about 0.05 moles of promoter per mole of olefin, and at a ratio of ester to olefins of from about 0.001 moles to about 0.15 moles per mole of olefin. In preferred applications, the oligomerization is carried out in a promoter to olefin ratio of from about 0.002 moles to about 0.015 moles per mole of olefin, and in an ester to olefin ratio of from about 0.001 moles to about 0.075 moles per mole of olefin. Insofar as the oligomerization temperature is concerned, such temperature is generally employed in the range from about 0° C. to about 60° C. and preferably from about 10° C. to about 50° C. In another preferred modification, the aforementioned process is so conducted that monomer and dimer are first removed from the oligomerized olefin product by distillation and the remaining product thus obtained is then subjected to hydrogenation. The recovered monomer and dimer are recycled. In another modification only monomer is removed by distillation prior to hydrogenation. It is believed that the most significant phenomenon of the improved process of the present invention is the aforementioned transesterification which is temperature dependent. This transesterification is also related to the acid-strength of the promoter. At relatively high temperatures, above about °C, the transesterification is favored in accordance with the following reaction:

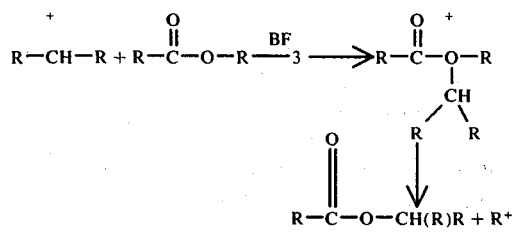

in which R is an alkyl group.

It would appear that, at higher temperatures, the transesterification discussed above interrupts the chain growth reaction leading to lower degrees of oligomerization. Conversely, at relatively lower temperatures where transesterification may not be important, the ester can serve as a promoter solvent resulting in higher than expected degrees of oligomerization. With respect to alcohol promoted boron fluoride, both temperature ranges fall within the scope of the invention. For water promoted catalyst, the low temperature promoter effect of ester is below the temperature range of the invention.

Regardless of the correct theoretical explanation, it is found that the present invention affords excellent yields of oligomer product having significantly lower viscosity at low temperature than is achieved with either ester alone or water/alcohol alone. This appears to be due to lower concentration in the product of oligomers higher than the trimer.

DESCRIPTION OF SPECIFIC EMBODIMENTS

As a prelude to examining specific embodiments of the invention, it is helpful to consider the effects of water or alcohol promoters and ester modifying agents separately as applied to the reactions with which the invention is concerned. Such consideration makes it possible to determine the extent, if any, to which the two types of agents act in additive manner. For that purpose, Examples 1 to 8 are to be considered as prefatory and not illustrative of the invention.

EXAMPLE 1

Decene-1 was charged, to a stirred flask which has been purged of air and the flask was cooled to 15° C., and pressured to about two inches of mercury with boron fluoride, together with 0.014 moles of methyl butyrate per hundred grams of olefin (0.02 moles of ester per mole of olefin). The reaction was maintained at 15° C for a total of 146 minutes from the initiation by start of addition to the flask. Net conversion of olefin to oligomers was 11.1% by weight on olefin charge. Degree of oligomerization was calculated as mean molecular weight of monomer free product divided by molecular weight of the monomer and found to be 2.45. Total yield of $C_{30}$ Plus product (trimer and heavier) was 4.6% by weight based on charge.

EXAMPLE 2

Since the yield of desired product from ester "activated" boron fluoride at 15° C was negligible (less than 5 wt.%) in Example 1, an attempt was made to obtain improved yield by increase of reaction temperature. This second run was conducted in the same manner as Example 1 with 0.013 moles of methyl butyrate per hundred moles of olefin at 100° C. Total conversion was raised slightly to 12.7 wt.% but degree of oligomerization was down to 2.27 and yield of $C_{30}$ Plus product was only 2 wt.% based on charge. Clearly, ester as promoter of boron fluoride for the present purpose is unavailing.

EXAMPLE 3

The reaction was conducted similarly to Example 1 at 15° C with 0.008 moles of water per hundred grams of decene-1. Net reaction time from start of addition was 104 minutes. Total conversion 97.4 wt.%. The oligomer was found to contain 4 wt.% dimer, 35 wt.% trimer and 61 wt.% heavier polymer for a $C_{30}$ Plus yield of 93.3 wt.%. KV of the dimer free product at −40° F was 5546 centipose, far too high for the contemplated use. Conceivably, this can be distilled to separate trimer as desired product, discarding higher polymer corresponding to about 60 wt.% of the expensive olefin feed, an obviously uneconomic expedient. In this, and in other examples, KV is reported on the raw oligomer (before hydrogenation). The comparisions so made are valid, since KV increases nearly uniformly by about 30% on hydrogenation.

EXAMPLE 4

Example 3 was repeated except that water concentration was 0.0085 moles per hundred grams of decene-1 and temperature was raised to 50° C. Total yield dropped to 97.0% (insignificant change) and $C_{30}$ Plus yield decreased to a value of 72.5 wt.%. Degree of oligomerization was 3.17. KV of $C_{30}$ Plus fraction at −40° F was 5692 centistokes, again unsuitable.

EXAMPLE 5

The temperature on this run was raised to 100° C for reaction time of 78 minutes with 0.008 moles of water per hundred grams of olefin for comparison against Examples 3 and 4. Total conversion dropped to 86.9 wt.% at 2.31 degree of oligomerization. Yield of $C_{30}$ Plus was only 23.0 wt.%.

EXAMPLE 6

A run was conductd with ethyl alcohol promoted boron fluoride at 15° C for a reaction time of 125 minutes. The alcohol promoter was present in the amount of 0.03 moles per hundred grams of decene-1. Total conversion was 99.4 wt.% with a $C_{30}$ Plus yield of 96.2. The latter showed a KV at −40° F of 5509.

EXAMPLE 7

A modest yield of desired product was obtained at 30° C with methyl alcohol in an amount of 0.008 moles per hundred moles of decene-1 as promoter for boron fluoride. Reaction time was 121 minutes. At total conversion of 71.0 wt.%, the $C_{30}$ Plus product was 46.9 wt.% on charge having KV at −40° F of 2291.

EXAMPLE 8

Yield with methyl alcohol promoted boron fluoride can be increased by raising the temperature. At 50° C, 114 minutes reaction time, 0.01 moles of methyl alcohol per hundred grams of decene-1, the total yield of oligomer was 98.5 wt.%; $C_{30}$ Plus yield of 66.8 wt.% based on charge. KV at −40° C of the $C_{30}$ Plus fraction was unsuitable at 4061.

It is clear that water or alcohol promotion alone is inadequate for the purpose stated within this temperature range. If adequate yields are obtained, oligomerization has proceeded too far. At lower yields, permitting expensive recycle of monomer and dimer, the bulk of the product is usually unsuited to the use intended. By way of control, addition of ester to the alcohol or water promoted boron fluoride controls the reaction, seemingly the opposite of additional promotion, such that the $C_{30}$ Plus fraction is an adequate yield of suitably low viscosity at $-40°$ F. These effects are dramatically illustrated in tabulated form below, where certain of the foregoing examples are included for comparison.

gratifying degree, this is accomplished by production of the desired trimer at the expense of higher oligomers. This effect is reflected in a dramatic reduction in Kinematic Viscosity of the $C_{30}$ Plus fraction at $-40°$ F. Because of increase in yield of dimer, which can be recycled with unreacted monomer, the yield of $C_{30}$ Plus product is reduced, but it will be seen that excellent net yields are attainable particularly at the lesser concentrations of ester.

EXAMPLES 13–16

TABLE 1

OLIGOMERIZATION OF DECENE-1

| EXAMPLE | 3 | 9 | 10 | 11 | 12 | 6 | 13 |
|---|---|---|---|---|---|---|---|
| Promoter | HOH | HOH | HOH | HOH | HOH | $C_2H_5OH$ | $C_2H_5OH$ |
| Moles* | 0.008 | 0.008 | 0.01 | 0.008 | 0.005 | 0.03 | 0.03 |
| Ester** | None | MB | MB | MB | MB | None | MB |
| Moles* | | 0.024 | 0.01 | 0.008 | 0.0025 | | 0.09 |
| Temp. ° C. | 15 | 15 | 15 | 15 | 25 | 15 | 15 |
| Time, mins. | 104 | 107 | 116 | 270 | 240 | 125 | 115 |
| Conv. wt.% | 97.4 | 93.1 | 94.3 | 98.8 | 96.0 | 99.4 | 51.1 |
| Dimer | 4 | 41 | 22 | 16 | 12 | 3 | 30 |
| Trimer | 35 | 52 | 64 | 64 | 63 | 34 | 63 |
| Residual | 61 | 7 | 14 | 20 | 25 | 63 | 7 |
| $C_{30}$ Plus Yield | 93.3 | 55 | 73.5 | 82.5 | 84.5 | 96.2 | 35.7 |
| KV,CS $-40°$ F. | 5546 | 2321 | 2367 | 2418 | — | 5509 | — |
| EXAMPLE | 14 | 15 | 16 | 7 | 8 | 17 | 18 |
| Promoter | $C_2H_5OH$ | $C_2H_5OH$ | $C_2H_5OH$ | $CH_3OH$ | $CH_3OH$ | $CH_3OH$ | $CH_3OH$ |
| Moles* | 0.03 | 0.03 | 0.03 | 0.008 | 0.01 | 0.01 | 0.01 |
| Ester** | MB | MV | EB | None | None | MB | MB |
| Moles* | 0.09 | 0.09 | 0.09 | | | 0.03 | 0.03 |
| Temp. ° C. | 15 | 15 | 15 | 30 | 50 | 30 | 50 |
| Time, mins. | 205 | 114 | 169 | 121 | 114 | 120 | 120 |
| Conv.wt.% | 91.9 | 78.5 | 74.8 | 71.0 | 98.5 | 99.1 | 75.4 |
| Dimer | 35 | 27 | 28 | 34 | 31 | 10 | 70 |
| Trimer | 60 | 68 | 66 | 52 | 50 | 59 | 29 |
| Residual | 5 | 5 | 6 | 14 | 18 | 31 | 1 |
| $C_{30}$ Plus Yield | 59.8 | 57.3 | 53.7 | 46.9 | 66.8 | 89.0 | 22.6 |
| KV,CS $-40°$ F. | 2256 | 1714 | 1744 | 2291 | 4061 | — | — |

*Moles of promoter or ester per mole of decene-1.
**Esters are designated by initials: Methyl Butyrate (MB), Ethyl Butyrate (EB), Mixed Methyl Valerate (MV).

As a prelude to review of the tabulated data, it is noted that although similar considerations apply to alcohol promoted and water promoted systems, these are seen at different temperatures for the two types of promoters. This is probably due to the different strengths of the Lewis acids generated by addition of alcohol or water to boron fluoride. Turning first to the water promoted system, temperatures above about $0°$ C result in reactions dominated by the transesterification effect discussed above. At lower temperatures, the solvent effect would be dominant. It is considered economically unattractive to maintain the very low temperatures needed for solvent effect when the desired end effect can be realized at the temperatures here shown.

EXAMPLES 9–12

These examples illustrate use of ester to modify water promoted boron fluoride oligomerization of decene-1 and are to be compared with Examples 3, 4 and 5. Example 3 is repeated in the tabulation for convenience. All five tabulated runs using water promoted boron trifluoride show very high levels of total conversion, about 93 to 99% of the olefin being oligomerized. The ester is clearly not affecting degree to which olefin is reacted. The feature of interest is nature of the oligomer. Presence of ester has served to limit the chain length, reduce the degree of oligomerization. To a These examples show the effect of different esters on boron fluoride oligomerization in the presence of ethanol as promoter. As compared with Example 6, ester is shown to limit the chain length to shift product to dimer and trimer at the expense of higher oligomer products. Again comparable total conversions are obtainable with and without ester. Compare Examples 6 and 14. Ester reduces $C_{30}$ Plus yield despite increase in trimer because the yield of oligomer higher than trimer is almost insignificant.

Comparison of Examples 13 and 14 is interesting as showing that increase of time of reaction increases total conversion for the conditions shown, but gives essentially the same product distribution. The reduced viscosity indicates suitability of the product resulting from ester modification as base for aircraft hydraulic fluid.

EXAMPLES 17–18

These show the effect of methyl butyrate at two temperatures on methanol promoter boron fluoride oligomerization of decene-1.

I claim:

1. In a process for preparing oligomers of aliphatic olefins having from about 6 to about 12 carbon atoms in the presence of boron fluoride promoted by a minor amount of alcohol or water, the improvement which comprises conducting the reaction at a temperature between about $0°$ C and about $60°$ C in the presence of a catalyst modifier which controls the reaction to reduce formation of oligomers higher than the trimer; said modifier being methyl or ethyl ester of a mono carboxylic acid having 2–5 carbon atoms in an amount of about 0.001 moles to about 0.075 moles of ester per mole of said alpha olefin.

2. A process in accordance with claim 1 wherein said oligomerization is carried out at a promoter (water or alcohol) to olefin ratio of from about 0.002 moles to about 0.015 moles of promoter per mole of olefin and an ester to olefin ratio of from about 0.001 moles to about 0.075 moles per mole of olefin.

3. A process in accordance with claim 1 wherein said oligomerization is carried out at a temperature from about 10° C. to about 50° C.

4. A process in accordance with claim 1 wherein said olefin is 1-decene.

5. A process in accordance with claim 1 wherein free monomer and dimer are removed from the oligomerized olefin product by distillation and the remaining product thus obtained is subjected to hydrogenation.

* * * * *